United States Patent
Sakai

(10) Patent No.: US 7,978,811 B2
(45) Date of Patent: Jul. 12, 2011

(54) RADIOGRAPHIC APPARATUS

(75) Inventor: Takihito Sakai, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 21 days.

(21) Appl. No.: 12/666,786

(22) PCT Filed: Jun. 29, 2007

(86) PCT No.: PCT/JP2007/063088
§ 371 (c)(1),
(2), (4) Date: Dec. 24, 2009

(87) PCT Pub. No.: WO2009/004677
PCT Pub. Date: Jan. 8, 2009

(65) Prior Publication Data
US 2010/0189336 A1  Jul. 29, 2010

(51) Int. Cl.
G01N 23/00 (2006.01)
G01N 23/04 (2006.01)
H05G 1/02 (2006.01)

(52) U.S. Cl. .............................. 378/21; 378/62; 378/196

(58) Field of Classification Search .................... 378/62, 378/21–27, 98.8, 196, 197
See application file for complete search history.

(56) References Cited

U.S. PATENT DOCUMENTS

| 5,631,942 | A | 5/1997 | Shinoda | |
|---|---|---|---|---|
| 6,659,641 | B2 * | 12/2003 | Schwieker | 378/196 |
| 2002/0006184 | A1 * | 1/2002 | Katoh et al. | 378/196 |
| 2004/0127789 | A1 | 7/2004 | Ogawa | |

FOREIGN PATENT DOCUMENTS

| JP | 6-285061 A | 10/1994 |
|---|---|---|
| JP | 2004-209239 A | 7/2004 |
| JP | 2004-236929 A | 8/2004 |
| JP | 2004-242928 A | 9/2004 |
| JP | 2005-46444 A | 2/2005 |
| JP | 2007-125102 A | 5/2007 |

OTHER PUBLICATIONS

The First Office Action for the Application No. 200780053588.5 from The State Intellectual Property Office of the People's Republic of China dated Oct. 11, 2010.
International Search Report for the Application No. PCT/JP2007/063088 mailed Oct. 2, 2007.

* cited by examiner

Primary Examiner — Irakli Kiknadze
(74) Attorney, Agent, or Firm — Cheng Law Group, PLLC

(57) ABSTRACT

In a radiographic apparatus of this invention, when obtaining a long image in a longitudinal direction, an image composing unit combines a plurality of radiographic images in the longitudinal direction based on detected radiation, and a setting unit sets a length of a radiographic image to be composed in the longitudinal direction. Therefore, with the setting unit setting the length of the radiographic image to be composed in the longitudinal direction, the length can be set without requiring an expansion or reduction of the radiographic image of a site of concern. The site of concern is constantly maintained on the same scale to reduce the chance of inducing errors.

4 Claims, 8 Drawing Sheets

RADIOGRAPHIC APPARATUS

TECHNICAL FIELD

This invention relates to radiographic apparatus for carrying out radiographic imaging, and more particularly to a technique in which a radiation emitting device and a radiation detecting device are movable parallel to each other in the same direction longitudinally of a subject.

BACKGROUND ART

Conventionally, there is an X-ray apparatus for obtaining a plurality of X-ray images along the body axis of a subject by moving an X-ray tube (radiation emitting device) and an X-ray detector (radiation detecting device) parallel to each other in the same direction along the body axis of the subject (see Patent Documents 1 and 2, for example). Based on the plurality of X-ray images obtained from this apparatus, an X-ray image of a long area (long X-ray image) can be obtained through composition in a longitudinal direction which is the direction of the body axis.

[Patent Document 1]
Unexamined Patent Publication No. 2004-242928 (pages 1-7, FIGS. 1, 6, 11 and 12)

[Patent Document 2]
Unexamined Patent Publication No. 2004-236929 (pages 1-8, FIGS. 1, 6 and 10)

DISCLOSURE OF THE INVENTION

Problem to be Solved by the Invention

The size (the length in the longitudinal direction) of the long X-ray image composed in this way is dependent on the size of the area which is actually imaged and collected. However, for cases such as scoliosis, imaging (examination) is carried out continually about twice a year for progress observation. In full lower limb radiography, examination is carried out a plurality of times for comparison purposes before and after medical treatment such as a surgical operation. However, the size of images may change because of growth of the patient or a misalignment at a setting time. Different size images produced in this way are not intuitive for comparative observation, and tend to induce errors where a comparison in size is important.

This invention has been made having regard to the state of the art noted above, and its object is to provide a radiographic apparatus for constantly assuring the same scale for a site of concern to reduce the chance of inducing errors.

Means for Solving the Problem

To fulfill the above object, this invention provides the following construction.

A radiographic apparatus of this invention is a radiographic apparatus having a radiation emitting device for emitting radiation toward a patient, and a radiation detecting device for detecting radiation transmitted through the patient, to carry out radiation image pickup by obtaining radiographic images based on the detected radiation, the radiation emitting device and the radiation detecting device being constructed movable parallel to each other in the same direction along a longitudinal direction of the patient, the radiation emitting device emitting radiation and the radiation detecting device detecting radiation transmitted through the patient irradiated while the radiation emitting device and the radiation detecting device move parallel to each other in the same direction relative to the patient, the apparatus comprising an image composing device for combining, in the longitudinal direction, a plurality of radiographic images based on radiation detected whenever a relative movement takes place in the same direction, and a setting device for setting a length of a radiographic image to be composed in the longitudinal direction, the apparatus further comprising an image joining device which, when a set length of the radiographic image in the longitudinal direction is longer than a length of a radiographic image in the longitudinal direction composed by the image composing device, joins in the longitudinal direction a dummy image having a difference in the longitudinal direction between the set length of the radiographic image and the length of the composed radiographic image, and the composed radiographic image.

According to the radiographic apparatus of this invention, the radiation emitting device and radiation detecting device are constructed movable parallel to each other in the same direction along the longitudinal direction of the patient, whereby data of a long field of view along the longitudinal direction can be obtained from the radiation detecting device. On the other hand, while the radiation emitting device and radiation detecting device move in the same direction relative to the patient, radiation is emitted from the radiation emitting device, and the radiation detecting device detects radiation transmitted through the irradiated patient. The image composing device combines, in the longitudinal direction, a plurality of radiographic images based on the radiation detected whenever the relative movement takes place in the same direction. The setting device sets a length of a radiographic image to be composed in the longitudinal direction. Therefore, with the setting device setting the length of the radiographic image to be composed in the longitudinal direction, the length can be set without requiring an expansion or reduction of the radiographic image of a site of concern. As a result, the site of concern is constantly maintained on the same scale to reduce the chance of inducing errors.

Further, the image joining device is provided for joining in the longitudinal direction a dummy image having a difference in the longitudinal direction between the above set length of the radiographic image and the above length of the composed radiographic image, and the composed radiographic image. With such image joining device, even when the set length of the radiographic image in the longitudinal direction is longer than the length of the composed radiographic image in the longitudinal direction, the insufficient length on the part of the composed radiographic image can be compensated for with the dummy image instead of expanding the composed radiographic image.

One example of the above dummy image is an image formed of pixels having a pixel value of a predetermined value. With the dummy image being an image formed of pixels having a pixel value of a predetermined value, the dummy image with a uniform pixel value can be joined with the radiographic image, to render the radiographic image and dummy image distinguishable. The above predetermined value is a value taking minimum luminance ("0" in the case of a positive image), and the dummy image is an image formed of black pixels. With the predetermined value being minimum luminance value "0", the pixels having a pixel value of the predetermined value become black pixels. The dummy image formed of the black pixels can be joined with the radiographic image, to render the radiographic image and dummy image all the more distinguishable.

A radiographic apparatus of a different invention is a radiographic apparatus having a radiation emitting device for emitting radiation toward a patient, and a radiation detecting device for detecting radiation transmitted through the patient, to carry out radiation image pickup by obtaining radiographic images based on the detected radiation, the radiation emitting device and the radiation detecting device being constructed movable parallel to each other in the same direction along a longitudinal direction of the patient, the radiation emitting device emitting radiation and the radiation detecting device detecting radiation transmitted through the patient irradiated while the radiation emitting device and the radiation detecting device move parallel to each other in the same direction relative to the patient, the apparatus comprising an image composing device for combining, in the longitudinal direction, a plurality of radiographic images based on radiation detected whenever a relative movement takes place in the same direction, and a setting device for setting a length of a radiographic image to be composed in the longitudinal direction, the apparatus further comprising an extending device which, when a set length of the radiographic image in the longitudinal direction is shorter than a length of a radiographic image in the longitudinal direction composed by the image composing device, extends the set length of the radiographic image to become the length of the composed radiographic image.

According to the radiographic apparatus of this invention, as in the former invention, the radiation emitting device and radiation detecting device are constructed movable parallel to each other in the same direction along the longitudinal direction of the patient, whereby data of a long field of view along the longitudinal direction can be obtained from the radiation detecting device. On the other hand, while the radiation emitting device and radiation detecting device move in the same direction relative to the patient, radiation is emitted from the radiation emitting device, and the radiation detecting device detects radiation transmitted through the irradiated patient. The image composing device combines, in the longitudinal direction, a plurality of radiographic images based on the radiation detected whenever the relative movement takes place in the same direction. The setting device sets a length of a radiographic image to be composed in the longitudinal direction. Therefore, with the setting device setting the length of the radiographic image to be composed in the longitudinal direction, the length can be set without requiring an expansion or reduction of the radiographic image of a site of concern. As a result, the site of concern is constantly maintained on the same scale to reduce the chance of inducing errors.

Further, the extending device is provided for extending the above set length of the radiographic image to become the length of the composed radiographic image. With such extending device, even when the set length of the radiographic image in the longitudinal direction is shorter than the length of the composed radiographic image in the longitudinal direction, the insufficient length on the part of the set length of the radiographic image can be extended for compensation instead of reducing the composed radiographic image. In addition, it ensures imaging of the extra length portion on the part of the composed radiographic image without reducing the composed radiographic image.

Effects of the Invention

With the radiographic apparatus according to this invention, the radiation emitting device and the radiation detecting device are constructed movable parallel to each other in the same direction along the longitudinal direction of a patient. While the radiation emitting device and radiation detecting device move in the same direction relative to the patient, radiation is emitted from the radiation emitting device, and the radiation detecting device detects radiation transmitted through the irradiated patient. The image composing device combines, in the longitudinal direction, a plurality of radiographic images based on the radiation detected whenever the relative movement takes place in the same direction. The setting device sets a length of a radiographic image to be composed in the longitudinal direction. Therefore, with the setting device setting the length of the radiographic image to be composed in the longitudinal direction, the length can be set without requiring an expansion or reduction of the radiographic image of a site of concern. The site of concern is constantly maintained on the same scale to reduce the chance of inducing errors.

Further, in the former invention provided with the image joining device for joining in the longitudinal direction a dummy image having a difference in the longitudinal direction between the above set length of the radiographic image and the above length of the composed radiographic image, and the composed radiographic image, even when the set length of the radiographic image in the longitudinal direction is longer than the length of the composed radiographic image in the longitudinal direction, the insufficient length on the part of the composed radiographic image can be compensated for with the dummy image instead of expanding the composed radiographic image.

Further, in the latter invention provided with the extending device for extending the above set length of the radiographic image to become the length of the composed radiographic image, even when the set length of the radiographic image in the longitudinal direction is shorter than the length of the composed radiographic image in the longitudinal direction, the insufficient length on the part of the set length of the radiographic image can be extended for compensation instead of reducing the composed radiographic image. In addition, it ensures imaging of the extra length portion on the part of the composed radiographic image without reducing the composed radiographic image.

DESCRIPTION OF REFERENCES

Figure 1:
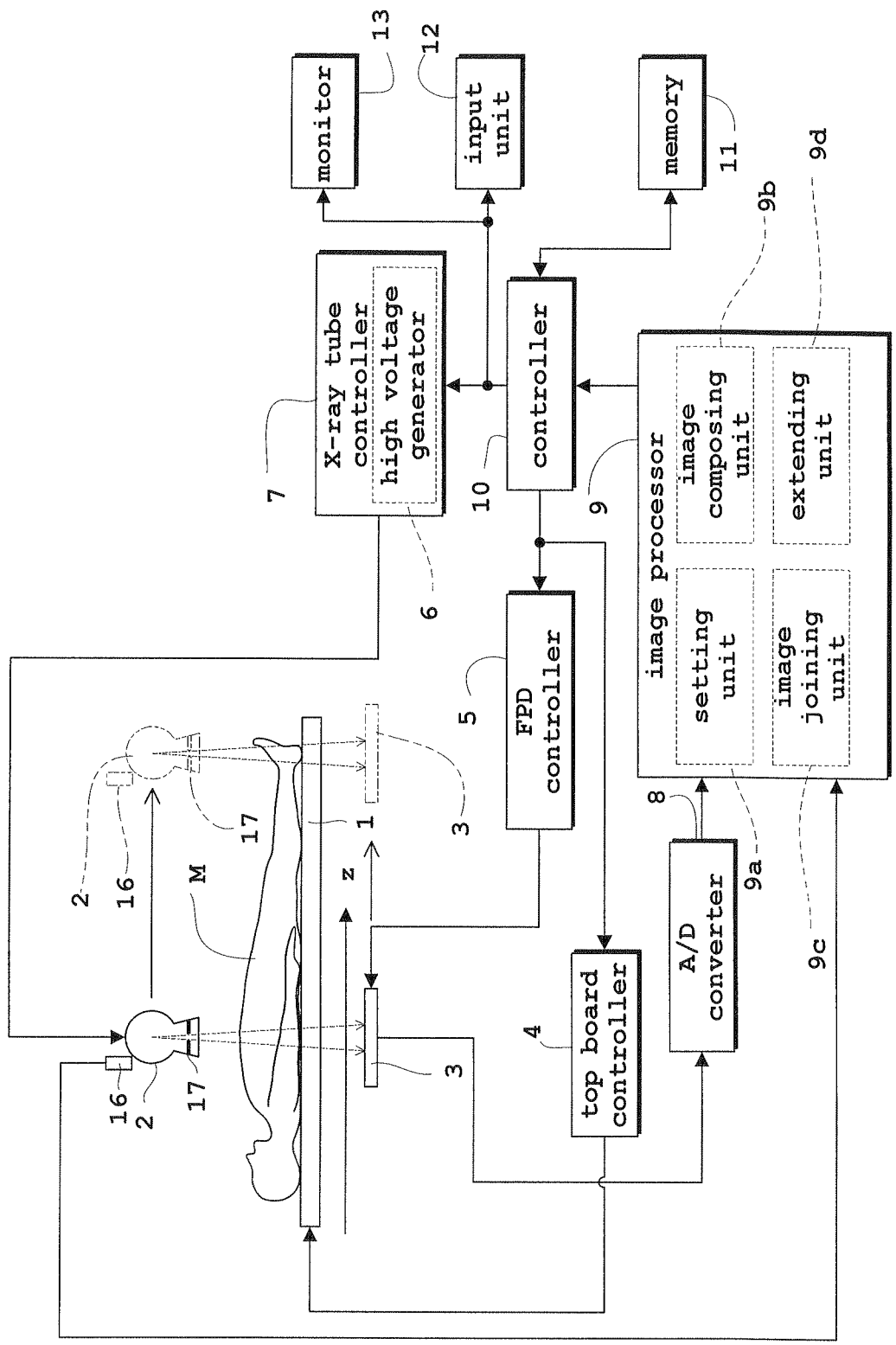
FIG. 1 is a block diagram of an X-ray imaging apparatus according to an embodiment.

2 . . . X-ray tube
3 . . . flat panel X-ray detector (FPD)
9a . . . setting unit
9b . . . image composing unit
9c . . . image joining unit
9d . . . extending unit
17 . . . collimator
z . . . body axis
M . . . patient

EMBODIMENT

Figure 2:
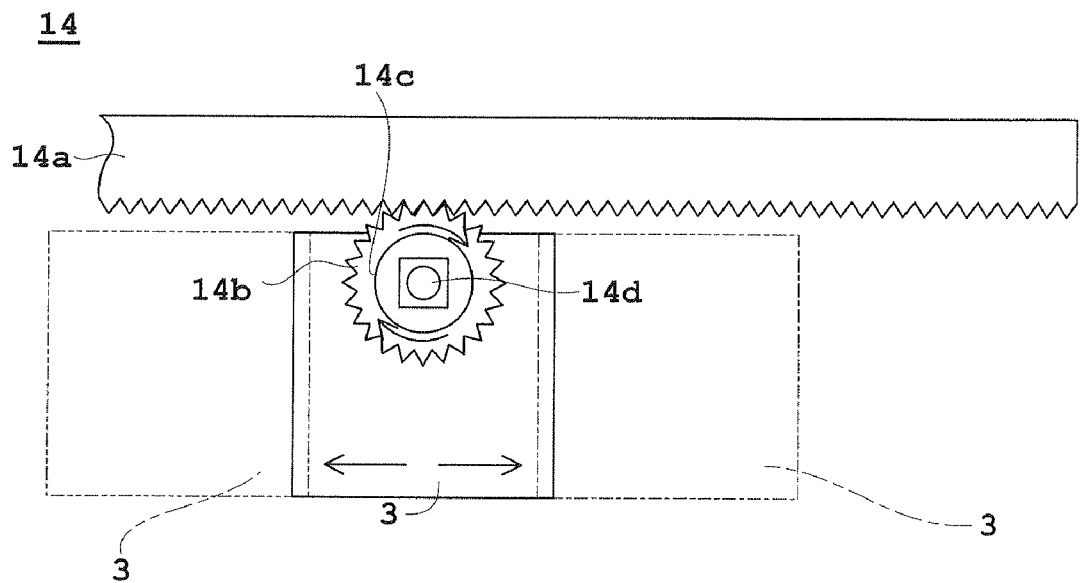
FIG. 2 is a schematic view showing an outline of an FPD drive mechanism relating to driving of a flat panel X-ray detector (FPD)
Figure 3:
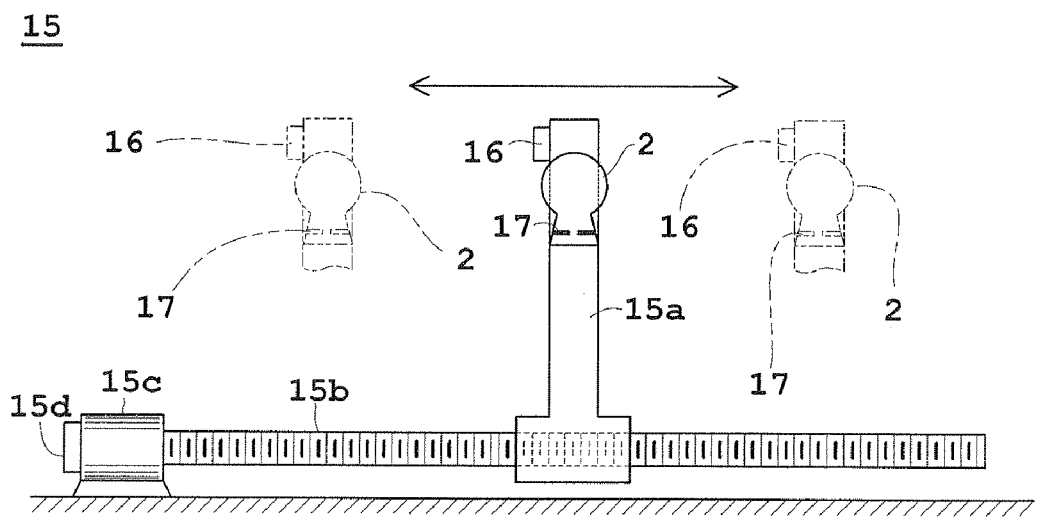
FIG. 3 is a schematic view showing an outline of an X-ray tube driver relating to driving of an X-ray tube.

An embodiment of this invention will be described hereinafter with reference to the drawings. FIG. 1 is a block diagram of an X-ray imaging apparatus according to the embodiment. FIG. 2 is a schematic view showing an outline of an FPD drive mechanism relating to driving of a flat panel X-ray detector. FIG. 3 is a schematic view showing an outline of an X-ray tube driver relating to driving of an X-ray tube. This embodiment will be described, taking the flat panel X-ray detector (hereinafter abbreviated as "FPD") as an example of radiation detecting device, and the X-ray imaging apparatus as an example of radiographic apparatus.

As shown in FIG. 1, the X-ray imaging apparatus includes a top board 1 for supporting a patient M, an X-ray tube 2 for emitting X rays toward the patient M, and an FPD 3 for detecting X-rays transmitted through the patient M. The X-ray tube 2 corresponds to the radiation emitting device in this invention. The FPD 3 corresponds to the radiation detecting device in this invention.

The X-ray imaging apparatus further includes a top board controller 4 for controlling vertical and horizontal movements of the top board 1, an FPD controller 5 for controlling scanning action of the FPD 3, an X-ray tube controller 7 having a high voltage generator 6 for generating a tube voltage and tube current for the X-ray tube 2, an analog-to-digital converter 8 for digitizing and fetching X-ray detection signals which are charge signals from the FPD 3, an image processor 9 for performing various processes based on the X-ray detection signals outputted from the analog-to-digital converter 8, a controller 10 for performing an overall control of these components, a memory 11 for storing processed images, an input unit 12 for the operator to input various settings, and a monitor 13 for displaying the processed images and other information.

The top board controller 4 controls movement of the top board 1, such as moving the top board 1 horizontally to place the patient M in an imaging position, vertically moving, rotating and horizontally moving the top board 1 to set the patient M to a desired position, horizontally moving the top board 1 during an imaging operation, and horizontally moving the top board 1 to withdraw the patient M from the imaging position after the imaging operation. These controls are carried out by controlling a top board driving mechanism (not shown) including motors and encoders (not shown).

The FPD controller 5 controls the FPD 3 to make parallel translation along the direction of a body axis z which is a longitudinal direction of the patient M. As shown in FIG. 2, this control is carried out by controlling an FPD drive mechanism 14 including a rack 14a, a pinion 14b, a motor 14c and an encoder 14d. Specifically, the rack 14a extends along the direction of body axis z of the patient M. The pinion 14b supports the FPD 3, is in part meshed with the rack 14a, and is rotatable by rotation of the motor 14c. For example, when the motor 14c is rotated forward, the FPD 3 will make parallel translation along the rack 14a toward the feet of the patient M as shown in the alternate long and short dash line in FIG. 2. When the motor 14c is reversed, the FPD 3 will make parallel translation along the rack 14a toward the head of the patient M as shown in the two-dot chain line in FIG. 2. The encoder 14d detects a direction of rotation and an amount of rotation of the motor 14c corresponding to a direction of movement and an amount of movement (moving distance) of the FPD 3. Results of detection by the encoder 14d are sent to the FPD controller 5.

The high voltage generator 6 generates the tube voltage and tube current for application to the X-ray tube 2 to emit X-rays. The X-ray tube controller 7 controls the X-ray tube 2 to make parallel translation along the direction of body axis z of the patient M. As shown in FIG. 3, this control is carried out by controlling an X-ray tube driver 15 including a strut 15a, a threaded rod 15b, a motor 15c and an encoder 15d. Specifically, the strut 15a carries and supports the X-ray tube 2 on an upper end portion thereof, and is screwed to the threaded rod 15b at a lower end portion. The threaded rod 15b extends along the direction of body axis z of the patient M and is rotatable by rotation of the motor 15c. For example, when the motor 15c is rotated forward, the X-ray tube 2 will make parallel translation with the strut 15a toward the feet of the patient M as shown in the alternate long and short dash line in FIG. 3. When the motor 15c is reversed, the X-ray tube 2 will make parallel translation with the strut 15a toward the head of the patient M as shown in the two-dot chain line in FIG. 3. The encoder 15d detects a direction of rotation and an amount of rotation of the motor 15c corresponding to a direction of movement and an amount of movement (moving distance) of the X-ray tube 2. Results of detection by the encoder 15d are sent to the X-ray tube controller 7.

In order to check the imaging position, a projector 16 is disposed on the strut 15a. With the projector 16 disposed, imaging is carried out by specifying an imaging start position, an imaging end position and so on. A collimator 17 is disposed at an emission side of the X-ray tube 2, which similarly is installed on the strut 15a, for controlling an irradiation field emitted from the X-ray tube 2. Arranged on the strut 15a, the projector 16 and collimator 17 also move with movement of the X-ray tube 2. With the collimator 22 operated for a restriction narrower than an irradiation field projected to the FPD 3 (see FIG. 1), the X-ray tube 2 and FPD 3 make parallel translation in the same direction along the direction of body axis z of the patient M as described hereinafter.

In order that the X-ray tube 2 and FPD 3 make parallel translation in the same direction along the direction of body axis z of the patient M as shown in FIG. 1, the FPD controller 5 and X-ray tube controller 7 carry out controls so that the direction of rotation of the motor 14c in FIG. 2 and the direction of rotation of the motor 15c in FIG. 3 may be the same. In this embodiment, it is preferred that the X-ray tube 2 and FPD 3 make parallel translation at an equal speed. That is, the FPD controller 5 controls the amount of rotation of the motor 14c and the X-ray tube controller 7 controls the amount of rotation of the motor 15c, so that the amount of movement of the X-ray tube 2 and the amount of movement of the FPD 3 may be the same.

The X-ray tube controller 7 controls the above-noted collimator 17 to control the irradiation field emitted from the X-ray tube 2 to be restricted narrower than the irradiation field projected to the FPD 3. The X-ray tube controller 7 controls the X-ray tube 2 to emit X-rays (in a slot form) with movement of the X-ray tube 2 and FPD 3. The FPD controller 5 controls the FPD 3 to detect X-rays transmitted through the patient M irradiated.

The controller 10 has a central processing unit (CPU) and other elements. The memory 11 has storage media, typically a ROM (Read-Only Memory) and RAM (Random Access Memory). The input unit 12 has a pointing device, typically a mouse, keyboard, joy stick, trackball and/or touch panel.

The image processor 9 includes a setting unit 9a for setting a length of an X-ray image to be composed in the direction of body axis z which is a longitudinal direction described hereinafter, an image composing unit 9b for combining, in the direction of body axis z which is the longitudinal direction, a plurality of X-ray images based on X-ray detection signals detected by the FPD 3 whenever the X-ray tube 2 and FPD 3 move in the same direction along the direction of body axis z of the patient M, an image joining unit 9c for joining a dummy image described hereinafter and a composed X-ray image in the direction of body axis z which is the longitudinal direction, and an extending unit 9d for extending the set length of the X-ray image to be the length of the composed X-ray image. The setting unit 9a corresponds to the setting device in this invention. The image composing unit 9b corresponds to the image composing device in this invention. The image joining unit 9c corresponds to the image joining device in this invention. The extending unit 9d corresponds to the extending device in this invention. Specific functions of the setting unit 9a, image composing unit 9b, image joining unit 9c and extending unit 9d will be described hereinafter with reference to FIGS. 6-9.

The memory 11 is constructed for writing and storing each image processed by the image processor 9. As does the controller 10, the FPD controller 5 and X-ray tube controller 7 also have CPUs and so on.

Figure 4:
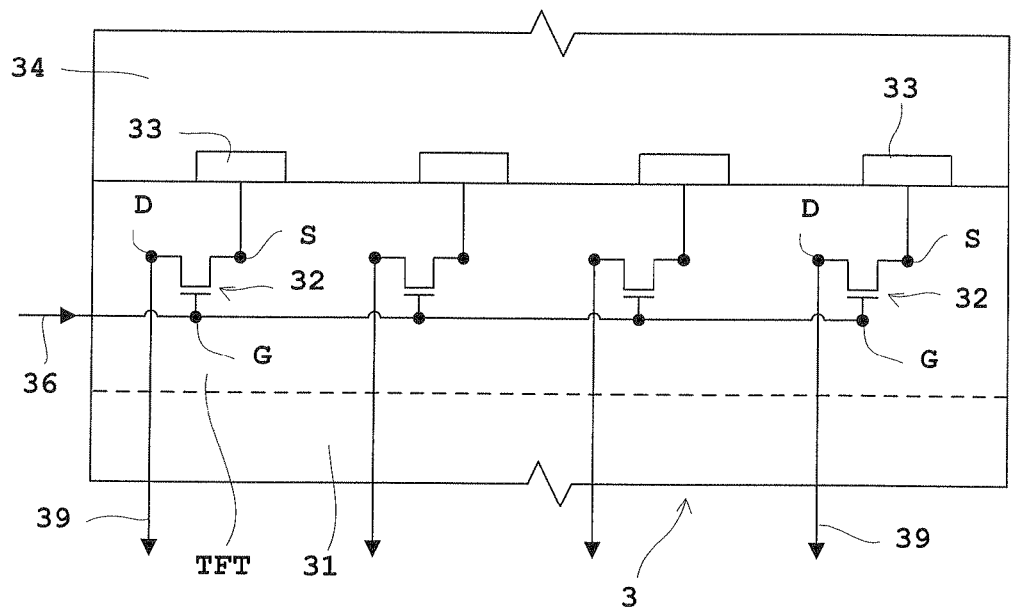
FIG. 4 is an equivalent circuit, seen in side view, of the flat panel X-ray detector (FPD)
Figure 5:
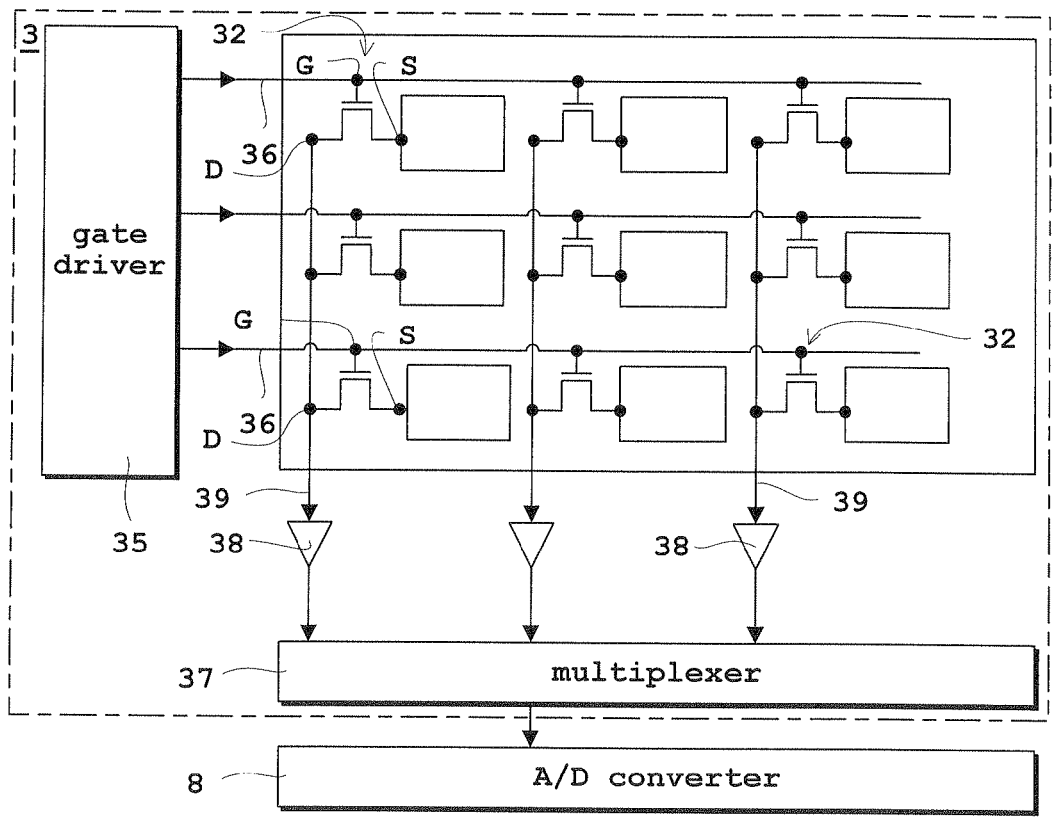
FIG. 5 is an equivalent circuit, seen in plan view, of the flat panel X-ray detector (FPD)

Next, the construction of the flat panel X-ray detector (FPD) 3 will be described with reference to FIGS. 4 and 5. FIG. 4 is an equivalent circuit, seen in side view, of the flat panel X-ray detector (FPD). FIG. 5 is an equivalent circuit, seen in plan view, of the flat panel X-ray detector (FPD).

As shown in FIG. 4, the FPD 3 includes a glass substrate 31, and thin film transistors TFT formed on the glass substrate 31. As shown in FIGS. 4 and 5, the thin film transistors TFT comprise numerous (e.g. 1,024×1,024) switching elements 32 arranged in a two-dimensional matrix of rows and columns. The switching elements 32 are formed separate from one another for respective carrier collecting electrodes 33. Thus, the FPD 3 is also a two-dimensional array radiation detector.

As shown in FIG. 4, an X-ray sensitive semiconductor 34 is laminated on the carrier collecting electrodes 33. As shown in FIGS. 4 and 5, the carrier collecting electrodes 33 are connected to the sources S of the switching elements 32. A plurality of gate bus lines 36 extend from a gate driver 35, and are connected to the gates G of the switching elements 32. On the other hand, as shown in FIG. 5, a plurality of data bus lines 39 are connected through amplifiers 38 to a multiplexer 37 for collecting charge signals and outputting as one. As shown in FIGS. 4 and 5, each data bus line 39 is connected to the drains D of the switching elements 32.

With a bias voltage applied to a common electrode not shown, the gates of the switching elements 32 are turned on by applying thereto (or reducing to 0V) the voltage of the gate bus lines 36. The carrier collecting electrodes 33 output charge signals (carriers) converted from X-rays incident on the detecting plane through the X-ray sensitive semiconductor 34, to the data bus lines 39 through the sources S and drains D of the switching elements 32. The charge signals are provisionally stored in capacitors (not shown) until the switching elements are turned on. The amplifiers 38 amplify the charge signals read out to the data bus lines 39, and the multiplexer 37 collects the charge signals, and outputs them as one charge signal. The analog-to-digital converter 8 digitizes the outputted charge signals, and outputs them as X-ray detection signals.

Figure 6:
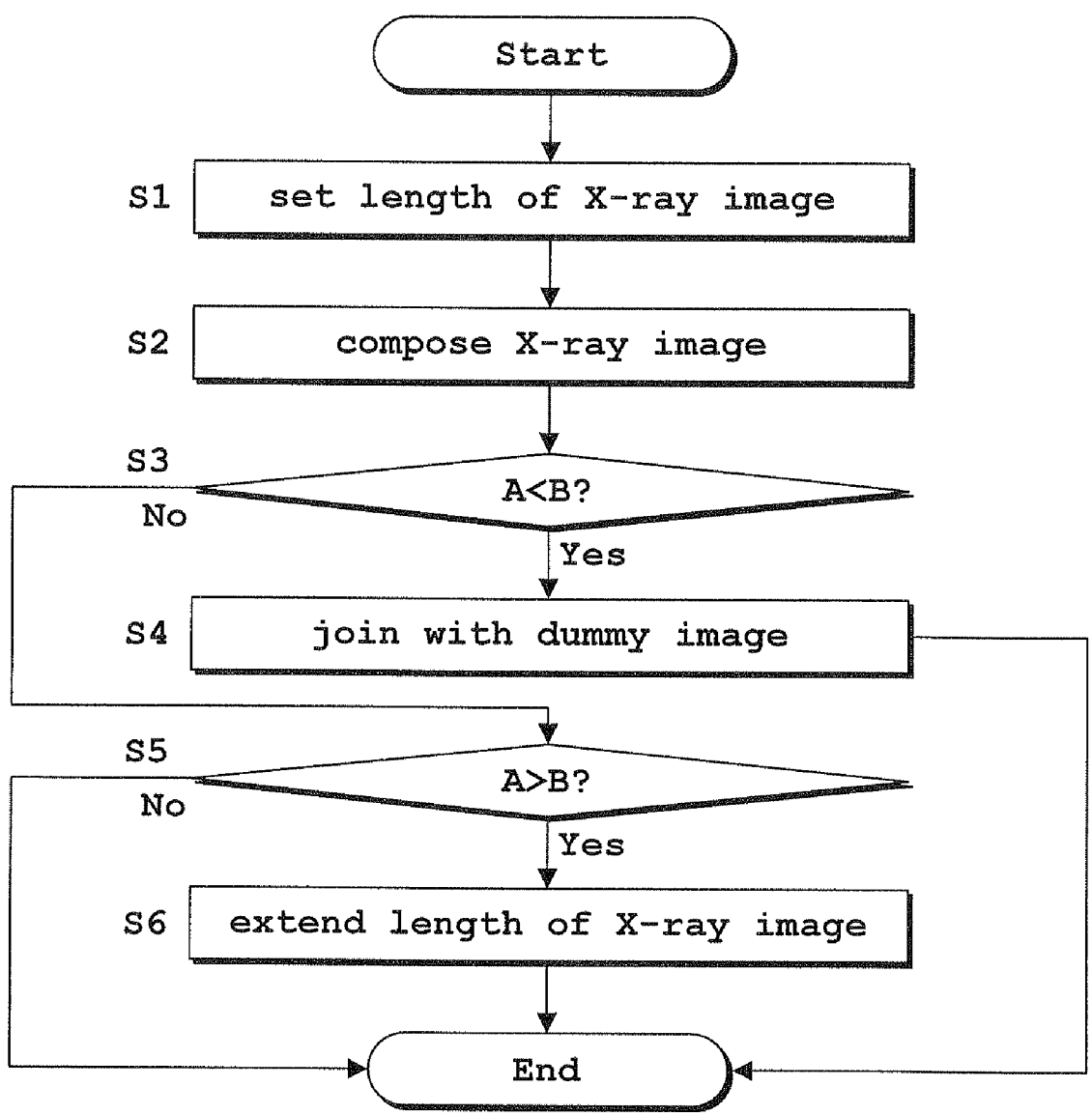
FIG. 6 is a flow chart of a series of image processes.
Figure 7:
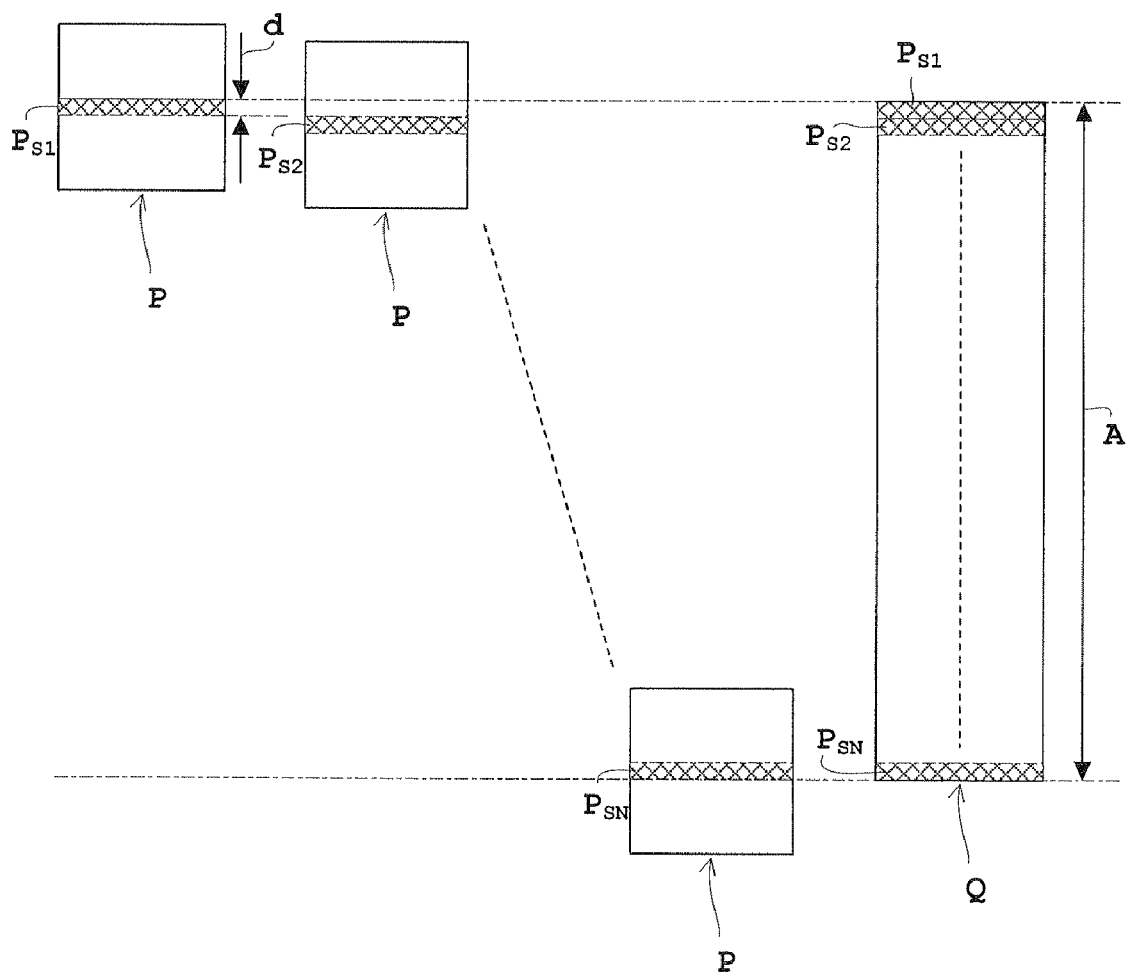
FIG. 7 is a schematic view of X-ray images before composition and after composition.
Figure 8:
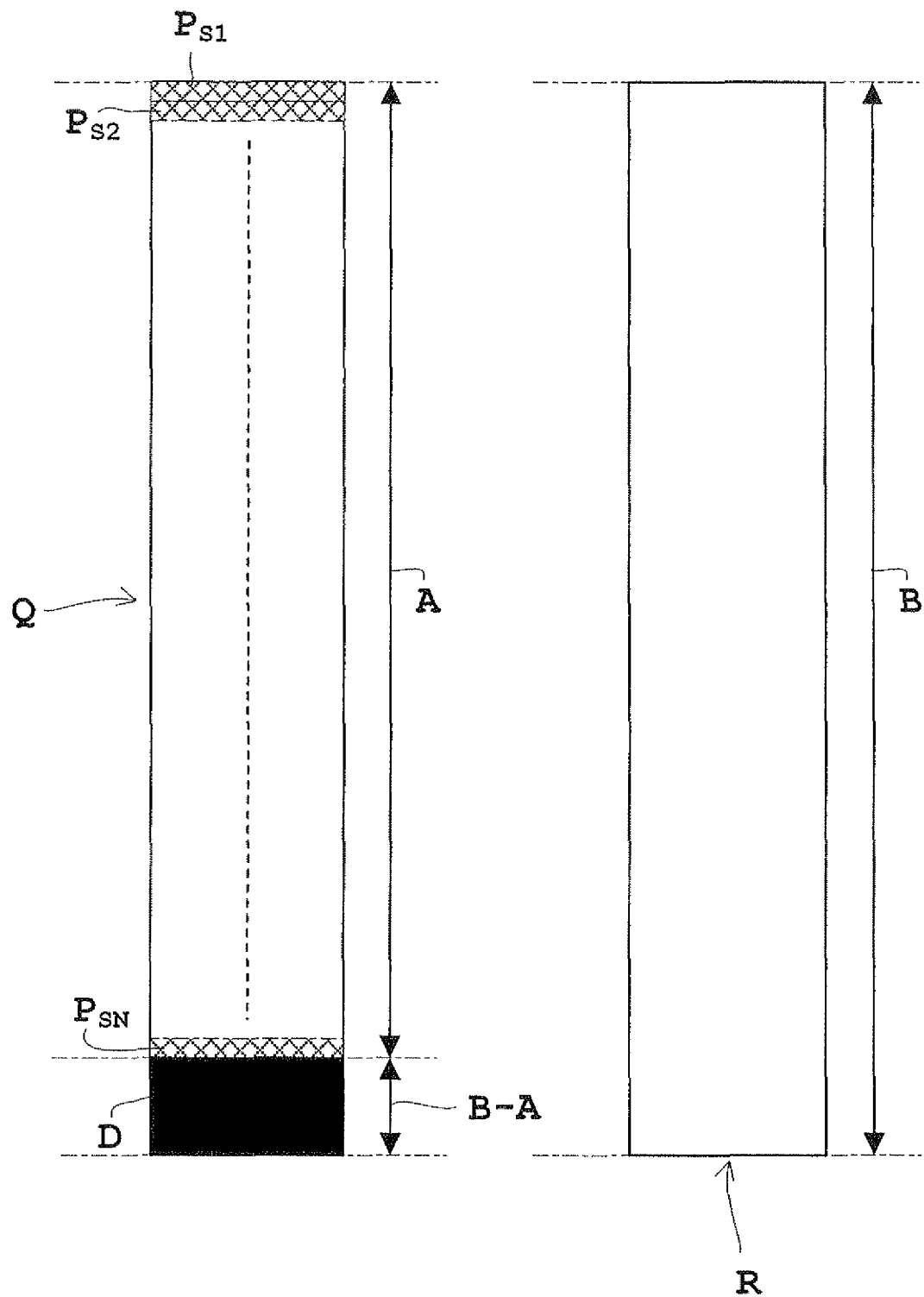
FIG. 8 is a schematic view showing joining with a dummy image where a set length of an X-ray image in the direction of a body axis is longer than a length of a composed X-ray image in the direction of the body axis.
Figure 9:
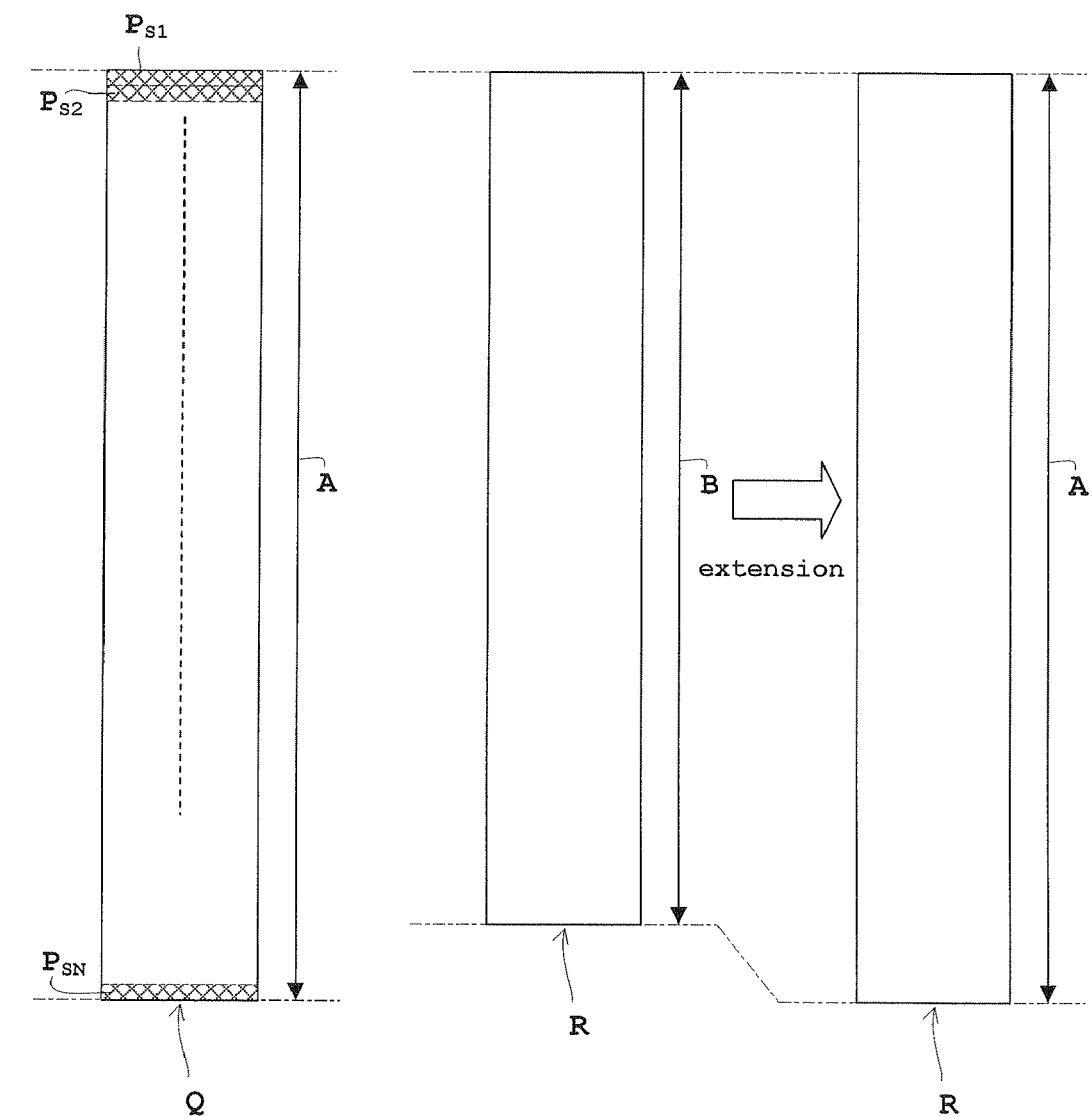
FIG. 9 is a schematic view showing extension of a set length of an X-ray image in the direction of the body axis where the set length of the X-ray image in the direction of the body axis is shorter than a length of a composed X-ray image in the direction of the body axis.

Next, specific functions of the setting unit 9a, image composing unit 9b, image joining unit 9c and extending unit 9d will be described with reference to FIGS. 6-9. FIG. 6 is a flow chart of a series of image processes. FIG. 7 is a schematic view of X-ray images before composition and after composition. FIG. 8 is a schematic view showing joining with a dummy image where a set length of an X-ray image in the direction of the body axis is longer than a length of a composed X-ray image in the direction of the body axis. FIG. 9 is a schematic view showing an extension of a set length of an X-ray image in the direction of the body axis where the set length of the X-ray image in the direction of the body axis is shorter than a length of a composed X-ray image in the direction of the body axis.

(Step S1) Set Length of X-Ray Image

The setting unit 9a sets a length of an X-ray image to be composed in the direction of body axis z which is the longitudinal direction. Where, as shown in FIG. 8, A is a length of X-ray image Q in the direction of body axis z composed by the image composing unit 9b in step S2 described hereinafter, and B is the length of X-ray image R in the direction of body axis z set by the setting unit 9a, $A \leq B$ is set in order to allow leeway for the length of X-ray image Q to be composed. That is, in view of growth of the patient M, the length B of X-ray image R in the direction of body axis z set by the setting unit 9a is made longer than the length A of X-ray image Q to be composed in the direction of body axis z even if the latter should increase to a certain extent. When, for example, a 1,000 mm area is radiographed, the length A of X-ray image Q to be composed in the direction of body axis z is set to 1,000 mm, and the setting unit 9a sets the length B of the X-ray image in the direction of body axis z to 1,050 mm, for example, in order to meet A<B.

(Step S2) Compose X-Ray Image

The width of an irradiation field emitted from the X-ray tube 2 and projected to the FPD 3 as restricted by the collimator 22 to be narrower than an irradiation field projected to the FPD 3 is called "slot width", and the slot width is set to d as shown in FIG. 7. With the irradiation field restricted to the slot width d in this way, imaging is carried out continuously in one operation in which the X-ray tube 2 and FPD 3 move in the same direction along the direction of body axis z of the patient M, the FPD 3 detects X-rays transmitted through the irradiated patient M, and a plurality of X-ray images are acquired based on the detected X-ray detection signals. That is, while the X-ray tube 2 and FPD 3 move in the same direction relative to the patient M, X-rays are emitted from the X-ray tube 2, and the FPD 3 detects X-rays transmitted through the irradiated patient M. Based on the X-ray detection signals detected whenever the X-ray tube 2 and FPD 3 move in the same direction, a plurality of X-ray images are obtained whenever the movement takes place.

A length from an imaging start position to an imaging end position is specified, and an imaging operation is completed when the projector 16 has moved from the imaging start position to the imaging end position. Alternatively, a length from an imaging start position to an imaging end position is specified, and an imaging operation is completed when the encoder 14d has detected the amount of rotation of the motor 14c of the FPD drive mechanism 14 or the amount of rotation of the motor 15*c* of the X-ray tube driver 15 which corresponds to that length. Through this series of imaging, N X-ray images P ($P_{S1}$, $P_{S2}$, . . . , $P_{SN}$) are acquired as shown in FIG. 7.

As shown in FIG. 7, the X-ray image P obtained with a slot width in the imaging start position becomes X-ray image $P_{S1}$ having slot width d. The X-ray image P obtained with a slot width in a next imaging position also becomes X-ray image $P_{S2}$ having slot width d. With the same operation thereafter repeated n times, the X-ray image P obtained with a slot width in the imaging end position will also become X-ray image $P_{SN}$ having slot width d. Therefore, length d×N from the imaging start position to the imaging end position becomes equal to length A of composed X-ray image Q in the direction of body axis z (d×N=A).

When the image composing unit 9*b* combines such N X-ray images P ($P_{S1}$, $P_{S2}$, . . . , $P_{SN}$) in the direction of body axis z, the X-ray image Q as shown in FIG. 7 is created. When, for example, slot width d is 20 mm and a 1,000 mm area is radiographed, N becomes 50 (=1,000 mm/20 mm=A/d) since the length A of the composed X-ray image Q in the direction of body axis z is 1,000 mm.

(Step S3) A<B?

When, as noted hereinbefore, the setting unit 9*a* sets the length B of the X-ray image to 1,050 mm for radiographing the 1,000 mm area, as shown in FIG. 8, the length B of X-ray image R in the direction of body axis z set by the setting unit 9*a* in step S1 becomes longer than the length A of X-ray image Q in the direction of body axis z composed by the image composing unit 9*b* in step S2 (A<B). When A<B, the operation proceeds to the next step S4. When A≧B, the operation proceeds to step S5.

(Step S4) Join with Dummy Image

When the set length B of the X-ray image in the direction of body axis z is determined in step S3 to be longer than the length A of the composed X-ray image in the direction of body axis z, as shown in FIG. 8, the image joining unit 9*c* joins, in the direction of body axis z which is the longitudinal direction, a dummy image D having the difference (B−A), in the direction of body axis z which is the longitudinal direction, between the set length B of the X image and the length A of the composed X-ray image, and the composed X-ray image Q. When the setting unit 9*a* sets the length B of the X-ray image to 1,050 mm for radiographing the 1,000 mm area as noted above, the length (B−A) of dummy image D in the direction of body axis z is 50 mm. Then, the series of image processing is completed.

In this embodiment, the dummy image D is an image formed of pixels having a pixel value of a predetermined value. In particular, the predetermined value, preferably, is a minimum luminance value ("0" in the case of a positive image). With the dummy image D being an image formed of pixels having a pixel value of a predetermined value, the dummy image D with a uniform pixel value can be joined with the X-ray image Q, to render the X-ray image Q and dummy image D distinguishable. With the predetermined value being a minimum luminance value, the pixels having a pixel value of the predetermined value become black pixels. The dummy image D formed of the black pixels can be joined with the X-ray image Q, to render the X-ray image Q and dummy image D all the more distinguishable.

The predetermined value is not limited to the minimum luminance value. In the case of a maximum luminance value ("4,095" in the case of a 12-bit positive image), the dummy image D is an image formed of white pixels. In the case of a predetermined value between the maximum luminance value and minimum luminance value, the dummy image D is an image formed of gray pixels. The dummy image D is not limited to an image formed of pixels having a pixel value of a predetermined value. For example, the dummy image D may be formed by arranging, in lattice form, pixels having a pixel value of predetermined minimum luminance value and maximum luminance value. However, considering distinguishment between the X-ray image Q and dummy image D, the dummy image D, preferably, is an image formed of pixels having a pixel value of a predetermined value. Furthermore, considering distinguishment between the X-ray image Q and dummy image D with increased reliability, it is more desirable that the predetermined value is a minimum luminance value, and that the dummy image D is an image formed of black pixels.

(Step S5) A>B?

When the setting unit 9*a* sets the length B of the X-ray image to 1,050 mm for radiographing a 1,100 mm area, as shown in FIG. 9, the length B of X-ray image R in the direction of body axis z set by the setting unit 9*a* in step S1 becomes shorter than the length A of X-ray image Q in the direction of body axis z composed by the image composing unit 9*b* in step S2 (A>B). When A>B, the operation proceeds to the next step S6. When A=B, the series of image processing is completed.

(Step S6) Extend Length of X-Ray Image

When the set length B of the X-ray image in the direction of body axis z is determined in steps S3 and S5 to be shorter than the length A of the composed X-ray image in the direction of body axis z, as shown in FIG. 9, the extending unit 9*d* extends the set length B of the X-ray image to the length A to become the length A of the composed X-ray image Q. When the setting unit 9*a* sets the length B of the X-ray image to 1,050 mm for radiographing the 1,100 mm area as noted above, the composed X-ray image Q is not reduced but maintained at 1,100 mm. On the other hand, when the set length B of the X-ray image is 1,050 mm, it is extended to the length A of 1,100 mm. Then, the series of image processing is completed.

According to the X-ray imaging apparatus in this embodiment, the X-ray tube 2 and flat panel X-ray detector (FPD) 3 are constructed to make parallel translation in the same direction along the body axis z which is the longitudinal direction of the patient M, whereby data of a long field of view along the body axis z which is the longitudinal direction can be obtained from the FPD 3. On the other hand, while the X-ray tube 2 and FPD 3 move in the same direction relative to the patient M, X-rays are emitted from the X-ray tube 2, and the FPD 3 detects X-rays transmitted through the irradiated patient M. The image composing unit 9*b* combines, in the direction of body axis z which is the longitudinal direction, a plurality of X-ray images based on X-ray detection signals detected whenever the movement takes place in the same direction. The setting unit 9*a* sets a length of an X-ray image to be composed in the direction of body axis z which is the longitudinal direction. Therefore, with the setting unit 9*a* setting the length of the X-ray image to be composed in the direction of body axis z which is the longitudinal direction, the length can be set without requiring an expansion or reduction of the X-ray image of a site of concern. As a result, the site of concern is constantly maintained on the same scale to reduce the chance of inducing errors.

In this embodiment, the arrangement is made as shown in FIG. 1 in case the length of an X-ray image in the direction of body axis z set by the setting unit 9*a* is longer than the length of an X-ray image in the direction of body axis z composed by the image composing unit 9*b*. That is, the image joining unit 9*c* is provided for joining, in the direction of body axis z, the dummy image having the difference, in the direction of body axis z, between the set length of the X image and the length of the composed X-ray image, and the composed X-ray image. With such image joining unit 9c, even when the set length of the X-ray image in the direction of body axis z is longer than the length of the composed X-ray image in the direction of body axis z, the insufficient length (see "B–A" in FIG. 8) on the part of the composed X-ray image can be compensated for with the dummy image instead of expanding the composed X-ray image.

In this embodiment, the arrangement is made as shown in FIG. 1 in case the length of an X-ray image in the direction of body axis z set by the setting unit 9a is shorter than the length of an X-ray image in the direction of body axis z composed by the image composing unit 9b. That is, the extending unit 9d is provided for extending the set length of the X-ray image to become the length of the composed X-ray image. With such extending unit 9d, even when the set length of the X-ray image in the direction of body axis z is shorter than the length of the composed X-ray image in the direction of body axis z, the insufficient length on the part of the set length of the X-ray image can be extended for compensation instead of reducing the composed X-ray image. In addition, it ensures imaging of the extra length portion on the part of the composed X-ray image without reducing the composed X-ray image.

In this embodiment, the X-ray tube 2 and FPD 3 make parallel translation at the same speed. With the X-ray tube 2 and FPD 3 making parallel translation at the same speed, a projection angle can be maintained at the same angle, and the X-ray tube 2 and FPD 3 can be moved longer. As a result, a composed X-ray image having a longer field of view can be obtained.

In this embodiment, the X-ray tube 2 has the collimator 17 attached thereto for controlling the irradiation field emitted from the X-ray tube 2 to be restricted narrower than the irradiation field projected to the FPD 3. With the irradiation field restricted to the slot width d by the collimator 17, the X-ray tube 2 and FPD 3 move parallel to each other in the same direction along the direction of body axis z of the patient M. In such a state of the irradiation field being restricted, imaging (i.e. slot imaging) is carried out continuously in one operation in which the X-ray tube 2 and FPD 3 move parallel to each other in the same direction along the direction of body axis z of the patient M, the FPD 3 detects X-rays transmitted through the irradiated patient M, and a plurality of X-ray images are acquired based on the detected X-ray detection signals.

This invention is not limited to the foregoing embodiment, but may be modified as follows:

(1) In the foregoing embodiment, the X-ray imaging apparatus has been described as an example of radiographic apparatus. The invention may be applied to a radiographic apparatus, such as an ECT (Emission Computed Tomography) apparatus represented by a PET (Positron Emission Tomography) apparatus or a SPECT (Single Photon Emission CT) apparatus, which carries out radiation image pickup by detecting radiation other than X-rays (gamma rays in the case of the PET apparatus) and obtaining radiographic images based on the detected radiation.

(2) In the foregoing embodiment, the flat panel X-ray detector has been described as an example of radiation detecting device. There is no limitation as long as the device is an X-ray detecting device used generally, such as an image intensifier (I.I). As in the case of being applied to an ECT apparatus, as in modification (1) above, there is no limitation as long as it is a radiation detecting device used generally.

(3) In the foregoing embodiment, the radiation emitting device represented by the X-ray tube 2 and the radiation detecting device represented by the FPD 3 are moved parallel to each other at the same speed. As long as the radiation emitting device and radiation detecting device are moved parallel relative to each other in the same direction along the longitudinal direction of the patient, one of them may be moved fast and the other moved slowly.

(4) In the foregoing embodiment, only the radiation emitting device represented by the X-ray tube 2 and the radiation detecting device represented by the FPD 3 are moved, and the top board 1 supporting the patient M is fixed, whereby the radiation emitting device and radiation detecting device are moved parallel to each other in the same direction along the longitudinal direction of the patient. The invention is not limited to a specific movement as long as the radiation emitting device and radiation detecting device are moved parallel to each other in the same direction along the longitudinal direction of the patient. For example, the radiation emitting device represented by the X-ray tube 2 and the radiation detecting device represented by the FPD 3 may be fixed, and only the top board 1 supporting the patient M may be moved, whereby the radiation emitting device and radiation detecting device are moved parallel to each other in the same direction along the longitudinal direction of the patient. The radiation emitting device represented by the X-ray tube 2 and the radiation detecting device represented by the FPD 3 may be moved, and the top board 1 supporting the patient M may also be moved in the longitudinal direction, whereby the radiation emitting device and radiation detecting device are moved parallel to each other in the same direction along the longitudinal direction of the patient.

Figure 10:
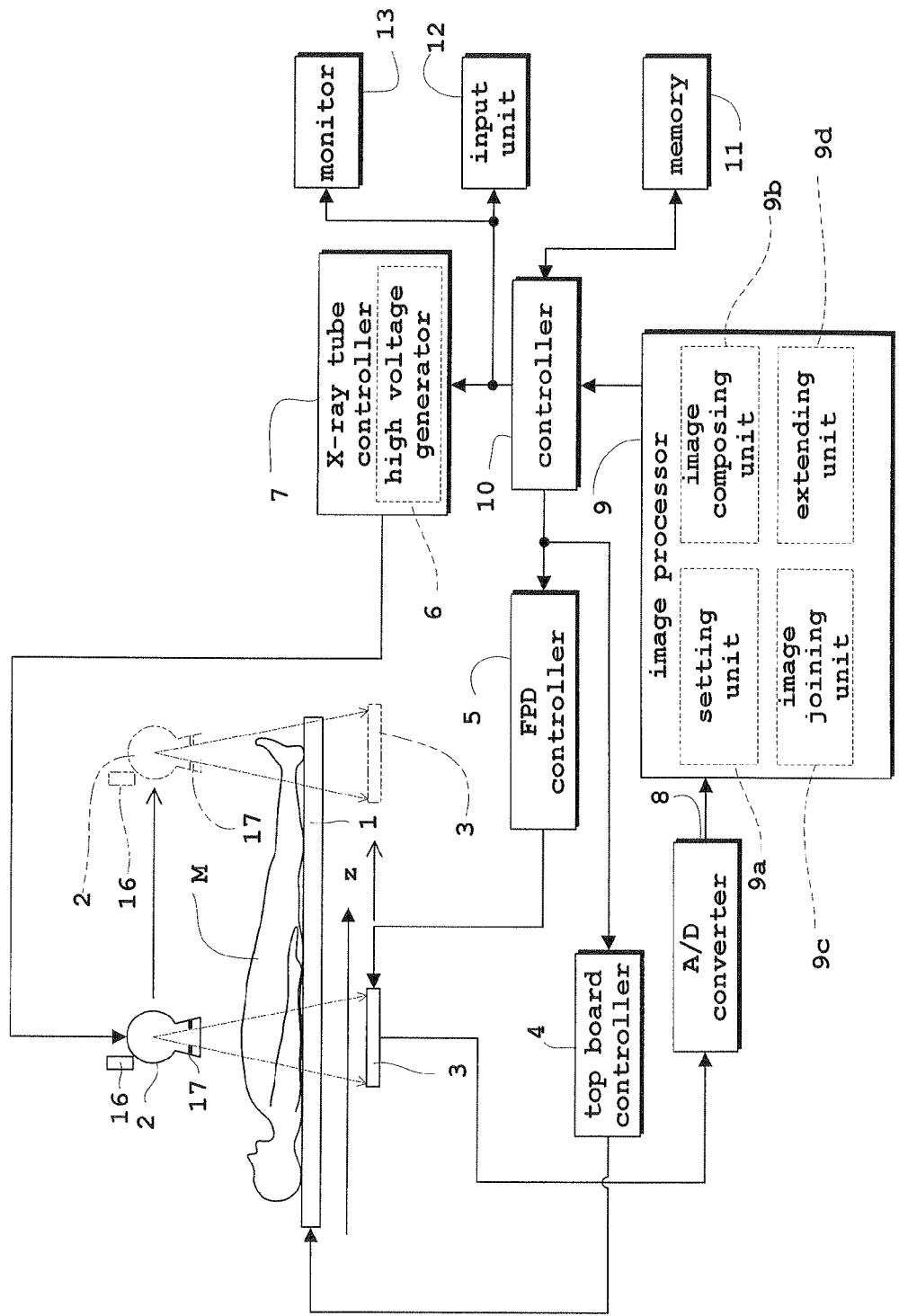
FIG. 10 is a block diagram of a modified X-ray imaging apparatus.

(5) The foregoing embodiment has been described taking for example the slot imaging with the irradiation field restricted narrow. As shown in the block diagram of FIG. 10, a normal imaging may be employed in which the radiation emitting device represented by the X-ray tube 2 provides an emission similar to the irradiation field projected to the radiation detecting device represented by the FPD 3. Apart from the irradiation field emitted from the X-ray tube 2, the block diagram of FIG. 10 shows the same construction as in the block diagram of FIG. 1, and thus its description is omitted.

The invention claimed is:

1. A radiographic apparatus having a radiation emitting device for emitting radiation toward a patient, and a radiation detecting device for detecting radiation transmitted through the patient, to carry out radiographic imaging by obtaining radiographic images based on the detected radiation, the radiation emitting device and the radiation detecting device being constructed movable parallel to each other in the same direction along a longitudinal direction of the patient, the radiation emitting device emitting radiation and the radiation detecting device detecting radiation transmitted through the patient irradiated while the radiation emitting device and the radiation detecting device move parallel to each other in the same direction relative to the patient, the apparatus comprising an image composing device for combining, in the longitudinal direction, a plurality of radiographic images based on radiation detected whenever a relative movement takes place in the same direction, and a setting device for setting a length of a radiographic image to be composed in the longitudinal direction, the apparatus further comprising an image joining device which, when a set length of the radiographic image in the longitudinal direction is longer than a length of a radiographic image in the longitudinal direction composed by the image composing device, joins in the longitudinal direction a dummy image having a difference in the longitudinal direction between the set length of the radiographic image and the length of the composed radiographic image, and the composed radiographic image.

2. The radiographic apparatus according to claim 1, wherein the dummy image is an image formed of pixels having a pixel value of a predetermined value.

3. The radiographic apparatus according to claim 2, wherein the predetermined value is a minimum luminance value, and the dummy image is an image formed of black pixels.

4. A radiographic apparatus having a radiation emitting device for emitting radiation toward a patient and a radiation detecting device for detecting radiation transmitted through the patient, to carry out radiographic imaging by obtaining radiographic images based on the detected radiation, the radiation emitting device and the radiation detecting device being constructed movable parallel to each other in the same direction along a longitudinal direction of the patient, the radiation emitting device emitting radiation and the radiation detecting device detecting radiation transmitted through the patient irradiated while the radiation emitting device and the radiation detecting device move parallel to each other in the same direction relative to the patient, the apparatus comprising an image composing device for combining, in the longitudinal direction, a plurality of radiographic images based on radiation detected whenever a relative movement takes place in the same direction, and a setting device for setting a length of a radiographic image to be composed in the longitudinal direction, the apparatus further comprising an extending device which, when a set length of the radiographic image in the longitudinal direction is shorter than a length of a radiographic image in the longitudinal direction composed by the image composing device, extends the set length of the radiographic image to become the length of the composed radiographic image.

* * * * *